United States Patent [19]

Karrenbauer et al.

[11] Patent Number: 4,550,199

[45] Date of Patent: Oct. 29, 1985

[54] PROCESS FOR OBTAINING D,L-HOMOCYSTINE (I)

[75] Inventors: Michael Karrenbauer, Rodenbach; Axel Kleemann, Hanau; Theodor Lüssling, Konstanz-Litzelstetten; Fritz Schäfer, Constance, all of Fed. Rep. of Germany

[73] Assignee: Degussa Aktiengesellschaft, Frankfurt, Fed. Rep. of Germany

[21] Appl. No.: 590,058

[22] Filed: Mar. 15, 1984

[30] Foreign Application Priority Data

Mar. 18, 1983 [DE] Fed. Rep. of Germany ....... 3309761

[51] Int. Cl.$^4$ ........................................ C07C 149/243
[52] U.S. Cl. .................................................. 562/556
[58] Field of Search .................... 562/557, 556; 568/26

[56] References Cited

FOREIGN PATENT DOCUMENTS 621915 4/1949 United Kingdom .

OTHER PUBLICATIONS

Reid, "Organic Chemistry of Bivalent Sulfur", vol. I, pp. 118–124 & 460–467, (1958).
Schoberl, Z. Physiol. Chem., 209, pp. 231–238, (1932).
Abderhalden, Chem. Abst., 18: 845, (1942).

Primary Examiner—Michael L. Shippen
Attorney, Agent, or Firm—Cushman, Darby & Cushman

[57] ABSTRACT

D,L-Homocystine is obtained by treating an aqueous solution of the disodium salt of D,L-homocysteine having a concentration between 0.4 and 1.6 moles/l and an initial pH between 7.0 and 8.0 under vigorous stirring with at least the equivalent amount of an aqueous solution of hydrogen peroxide and after the end of the oxidation adjusting the pH to about 5.3. The hydrogen peroxide solution can be employed with a concentration between 20 and 60 weight percent.

7 Claims, No Drawings

PROCESS FOR OBTAINING D,L-HOMOCYSTINE (I)

BACKGROUND OF THE INVENTION

The present invention is directed to a process for obtaining D,L-homocystine by oxidation of the disodium salt of D,L-homocysteine.

D,L-homocystine is of interest in the production of food for domestic animals.

Of course, it is known to oxidize mercaptans with hydrogen peroxide to the corresponding disulfides. In the case of D,L-homocysteine, however, there are obtained high yields of the desired D,L-homocystine only by maintaining specific conditions.

SUMMARY OF THE INVENTION

The process of the invention comprises obtaining D,L-homocystine by treating an aqueous solution of the disodium salt of D,L-homocysteine having a concentration between 0.4 and 1.6 moles/l and an inital pH between 7.0 and 8.0 under vigorous stirring with at least the equivalent amount of an aqueous solution of hydrogen peroxide and after the end of the oxidation adjusting the pH to about 5.3.

Surprisingly under these reaction conditions, the desired D,L-homocystine is obtained in yields of over 80%. In contrast if there is treated the aqueous solution of the disodium salt of D,L-homocysteine having a concentration of less than 0.4 mole/l or more than 1.6 moles/l or with an initial pH of less than 7.0 or more than 8.0 there are obtained clearly lower yields.

The aqueous solutions of the disodium salt of D,L-homocysteine serving as starting material can be produced in known manner by demethylation of D,L-methionine by means of sodium in liquid ammonia, subsequent vaporization of the ammonia and taking up the residue remaining in a suitable amount of water.

The adjustment of the initial pH to a value between 7.0 and 8.0 is carried out suitably with an aqueous mineral acid, preferably hydrochloric acid. However, other mineral acids can be used, e.g. sulfuric acid, hydrobromic acid, or phosphoric acid.

The aqueous hydrogen peroxide solution is suitably employed in the amount equivalent to the salt of the D,L-homocysteine. However, it is not disturbing to use a slight excess up to 5%. Preferably there are employed aqueous hydrogen peroxide solutions having a concentration between 20 and 60 weight percent. Since the oxidation reaction is strongly exothermic it is recommended to add the hydrogen peroxide solution slowly dropwise and to cool the reaction mixture during the addition. The oxidation reaction is generally ended when the total amount of hydrogen peroxide is added.

After the end of the oxidation the pH of reaction mixture is adjusted to about 5.3, suitably with an aqueous mineral acid, preferably hydrochloric acid. It is advantageous if the adjustment of the pH is carried out at elevated temperature, for example 50° C. and subsequently the reaction mixture is cooled to room temperature slowly with stirring, for example in the course of one hour. The D,L-homocystine is obtained in a particularly advantageous crystalline form if the stirring speed is regulated during the precipitation in such manner that the D,L-homocystine is obtained directly in suspension. Then it can be separated off especially easily by filtration or centrifugation.

Unless otherwise indicated all parts and percentages are by weight.

The process can comprise, consist essentially of, or consist of the stated steps with the recited materials.

The invention will be explained in more detail through the following examples and comparison experiments.

DETAILED DESCRIPTION

EXAMPLE 1

21.6 grams of the disodium salt of D,L-homocysteine produced by demethylation of D,L-methionine were dissolved in water and treated with hydrochloric acid so that there was formed a 0.4 molar solution having a pH of 7.0. This solution with indirect cooling wiht ice was treated dropwise with 6 ml of a 50% hydrogen peroxide solution with vigorous stirring. Subsequently the reaction mixture was heated to 50° C. and adjusted to a pH of 5.3 with 10% hydrochloric acid under stirring. Within one hour with stirring the mixture was cooled to room temperature. The precipitated D,L-homocystine was filtered off with suction, washed with 100 ml of water at 80° C. and dried in the vacuum drier until constant weight. The yield of D,L-homocystine with 14.7 grams, corresponding to 90.5% of theory.

EXAMPLE 2

Example 1 was repeated with the difference that the disodium salt of D,L-homocysteine was treated with sufficient water and hydrochloric acid that a 0.4 molar solution was formed having a pH of 8.0. The yield of D,L-homocystine was 13.3 grams corresponding to 81.7% of theory.

COMPARISON EXPERIMENT 1

Example 1 was repeated with the difference that the disodium salt of D,L-homocysteine was treated with sufficient water and hydrochloric acid that there was formed a 0.4 molar solution having a pH of 10.0. The yield of D,L-homocystine was 10.7 grams, corresponding to 65.7% of theory.

EXAMPLE 3

43.2 grams of the disodium salt of D,L-homocysteine produced by demethylation of D,L-methionine were dissolved in water and treated with hydrochloric acid so that there was formed a 0.8 molar solution having a pH of 7.0. This solution with indirect cooling with ice was treated with dropwise addition of 12 ml of 50% hydrogen peroxide solution with vigorous stirring and subsequently treated as in Example 1. The yield of D,L-homocystine was 29.3 grams, corresponding to 90.1% of theory.

EXAMPLE 4

Example 3 was repeated with the difference that the disodium salt of D,L-homocysteine was treated with sufficient water and hydrochloric acid that there was formed a 0.8 molar solution having a pH of 8.0. The yield of D,L-homocystine was 30.2 grams, corresponding to 93.0% of theory.

COMPARISON EXPERIMENT 2

Example 3 was repeated with the difference that the disodium salt of D,L-homocysteine was treated with sufficient water and hydrochloric acid that there was formed a 0.8 molar solution having a pH of 10.0. The yield of D,L-homocystine was 23.1 grams, corresponding to 71.0% of theory.

EXAMPLE 5

84.6 grams of the disodium salt of D,L-homocysteine produced by the demethylation of D,L-methionine were dissolved in water and treated with hydrochloric acid so that there was formed a 1.6 molar solution having a pH of 7.0. This solution with indirect cooling with ice was treated with dropwise addition of 24 ml of a 50% hydrogen peroxide solution under vigorous stirring and treated further as in Example 1. The yield of D,L-homocystine was 58.5 grams, corresponding to 90% of theory.

EXAMPLE 6

Example 5 was repeated with the difference that the disodium salt of D,L-homocysteine was treated with sufficient water and hydrochloric acid that there was formed a 1.6 molar solution having a pH of 8.0. The yield of D,L-homocystine was 60.0 grams, corresponding to 92.3% of theory.

COMPARISON EXPERIMENTS 3 to 5

Solutions of the same concentrations as in Example 5 but with initial pH values of 10.0, 11.0 and 12.0 were treated as in Example 5. The results are collected in the following Table:

| Initial pH | Yield |
| --- | --- |
| 10.0 | 47.5 grams (73.0% of theory) |
| 11.0 | 44.5 grams (68.5% of theory) |
| 12.0 | 34.5 grams (53.0% of theory) |

What is claimed is:

1. A process for obtaining D,L-homocystine by oxidation of the disodium salt of D,L-homocysteine comprising treating an aqueous solution of the disodium salt of D,L-homocysteine having a concentration between 0.4 and 1.6 moles/l and an initial pH between 7.0 and 8.0 under vigorous stirring with at least the equivalent amount of an aqueous solution of hydrogen peroxide and after the end of the oxidation adjusting the pH to about 5.3.

2. A process according to claim 1 wherein the hydrogen peroxide solution has a concentration between 20 and 60 weight percent.

3. A process according to claim 1 wherein the pH is adjusted to 5.3 at a temperature of about 50° C.

4. A process according to claim 1 wherein the sole materials employed are the disodium salt of D,L-homocysteine, water, hydrogen peroxide and mineral acid.

5. A process according to claim 4 wherein the mineral acid is sulfuric acid, hydrobromic acid, phosphoric acid or hydrochloric acid.

6. A process according to claim 5 wherein the mineral acid is hydrochloric acid.

7. A process according to claim 1 wherein the only present are sodium ions.

* * * * *